(12) United States Patent
Jirman et al.

(10) Patent No.: US 8,034,942 B2
(45) Date of Patent: Oct. 11, 2011

(54) PROCESS FOR THE PREPARATION OF SOLIFENACIN

(75) Inventors: Josef Jirman, Prague (CZ); Richard Junek, Prague (CZ); Petr Lustig, Pardubice (CZ); Jindrich Richter, Pardubice (CZ); Lukas Placek, Moravsky Kocov (CZ)

(73) Assignee: Zentiva k s., Prague (CZ)

( * ) Notice: Subject to any disclaimer, the term of this patent is extended or adjusted under 35 U.S.C. 154(b) by 355 days.

(21) Appl. No.: 12/305,452

(22) PCT Filed: Jun. 21, 2007

(86) PCT No.: PCT/CZ2007/000061
§ 371 (c)(1),
(2), (4) Date: Dec. 18, 2008

(87) PCT Pub. No.: WO2007/147374
PCT Pub. Date: Dec. 27, 2007

(65) Prior Publication Data
US 2009/0203914 A1    Aug. 13, 2009

(30) Foreign Application Priority Data
Jun. 21, 2006 (CZ) .............................. PV 2006 -407

(51) Int. Cl.
*C07D 453/04*    (2006.01)
(52) U.S. Cl. ....................................................... 546/134
(58) Field of Classification Search ............... 546/134
See application file for complete search history.

(56) References Cited

U.S. PATENT DOCUMENTS
2009/0326230 A1 * 12/2009 Mathad et al. ................ 546/137

FOREIGN PATENT DOCUMENTS
| EP | 0 801 067 | 10/1997 |
| EP | 1 726 304 | 11/2006 |
| WO | WO 96/20194 | 7/1996 |
| WO | WO 2005/087231 | 9/2005 |

OTHER PUBLICATIONS

Naito et al., Journal of Medicinal Chemistry (2005), 48(21), 6597-6606.*
International Search Report for International Application No. PCT/CZ2007/000061 mailed Feb. 25, 2008.

* cited by examiner

Primary Examiner — D M Seaman
Assistant Examiner — Niloofar Rahmani
(74) Attorney, Agent, or Firm — Pearl Cohen Zedek Latzer, LLP

(57) ABSTRACT

A process for the preparation of (1S)-QR)-I-azabicyclo [2.2.2.]oct-3-yl 3,4-dihydro-1-phenyl-2(1H)-isoquinoline carboxylate by reacting (1S)-alkyl 1-phenyl-1,2,3,4-tetrahydro-2-isoquinoline carboxylate with 3-(R)-quinuclidol in an inert solvent, where a primary alkyl ester of the carboxylate whose alkyl length is $C_1$-$C_4$ is used and the reaction is catalyzed by a non-nucleophilic base.

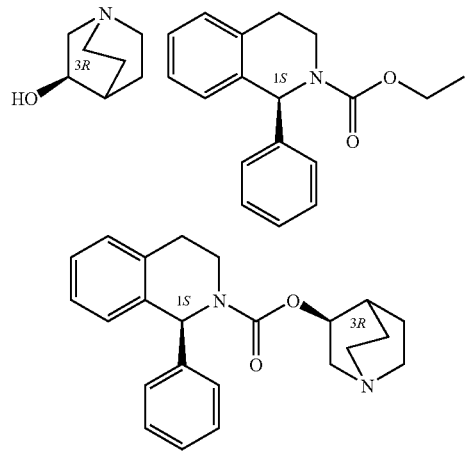

3 Claims, No Drawings

PROCESS FOR THE PREPARATION OF SOLIFENACIN

CROSS-REFERENCE TO RELATED APPLICATIONS

This application is a National Phase Application of PCT International Application No. PCT/CZ2007/000061, entitled "PROCESS FOR THE PREPARATION OF SOLIFENAON", International Filing Date Jun. 21, 2007, published on Dec. 27, 2007 as International Publication No. WO 2007/147374, which in turn claims priority from Czechoslovakian Patent Application No. PV 2006-407, filed Jun. 21, 2006, both of which are incorporated herein by reference in their entirety.

TECHNICAL FIELD

The invention relates to a new process of conducting the condensation of 3-(R)-quinuclidol of formula I and (1S)-ethyl 1-phenyl-1,2,3,4-tetrahydro-2-isoquinoline carboxylate of formula II to obtain (1S)-(3R)-1-azabicyclo[2.2.2.]oct-3-yl 3,4-dihydro-1-phenyl-2(1H)-isoquinoline carboxylate of formula III Formula I

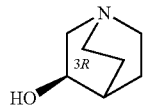

Formula II

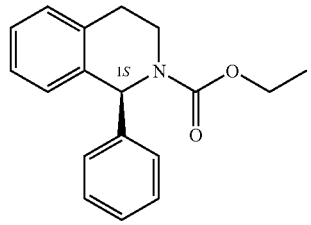

Formula III

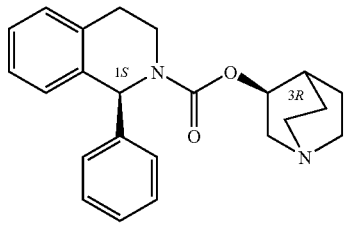

BACKGROUND ART

Original patent literature (EP 0 801 067, WO 9620194) describes a procedure where (1S)-ethyl 1-phenyl-1,2,3,4-tetrahydro-2-isoquinoline carboxylate is reacted with 3-(R)-quinuclidol, which is in about 290% theoretical amount, with sodium hydride, which is in about 156% theoretical amount, in a toluene suspension. The reaction mixture is refluxed, simultaneously distilling off the ethanol being formed, which leaves in the form of an azeotropic mixture with toluene. A reasonable degree of conversion is thereby attained. Nevertheless, the patent states that the yield is as modest as 56%.

The patent mentions also possibility of the synthesis procedure is mentioned where 1-phenyl-1,2,3,4-tetrahydro-2-isoquinoline carbonyl chloride of formula IV is reacted with 3-quinuclidol of formula V in dimethylformamide to obtain 1-azabicyclo[2.2.2.]oct-3-yl 3,4-dihydro-1-phenyl-2(1H)-isoquinoline carboxylate of formula VI.

Formula IV

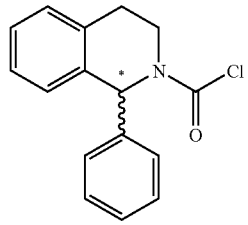

Formula V

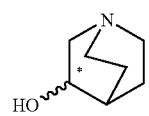

Formula VI

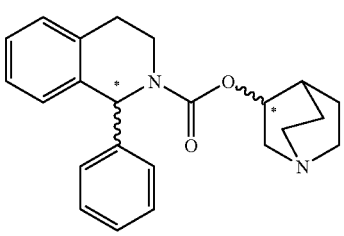

EP 0 801 067/WO 9620194 also report an arrangement where 3-(R)-quinuclidyl alkyl carbonate is allowed to react with 1-phenyl-1,2,3,4-tetrahydro-2-isoquinoline to give solifenacin.

Patent application WO 2005/087231 describes preparation of solifenacin by reacting (1S)-alkyl-1-phenyl-1,2,3,4-tetrahydro-2-isoquinoline carboxylate (where the alkyl is a lower alkyl, preferably methyl, ethyl, or benzyl) in a toluene-dimethylformamide mixture with 3-(R)-quinuclidol, the reaction being catalyzed by a sodium alkoxide, the alkoxide being so selected that its alkyl is identical with the alkyl of the (1S)-alkyl-1-phenyl-1,2,3,4-tetrahydro-2-isoquinoline carboxylate (hence, sodium methoxide, ethoxide, or benzyloxide).

We have found empirically that all the procedures published so far suffer from drawbacks. The procedure in EP 0 801 067 does not afford the product in a reasonably high yield and, in addition, uses a comparatively high excess of optically pure 3-(R)-quinuclidol which is rather costly.

The other route—reaction of 1-phenyl-1,2,3,4-tetrahydro-2-isoquinoline carbonyl chloride of formula IV with 3-quinuclidol of formula V in dimethylformamide, resulting in 1-azabicyclo[2.2.2.]oct-3-yl 3,4-dihydro-1-phenyl-2(1H)-isoquinoline carboxylate of formula VI—is mentioned in patent literature (EP 0 801 067) but no examples of the procedure are given. We have tested the procedure practically and found that, although the reaction between the two components, the carbamoyl chloride and quinuclidol, proceeds at a reasonably high rate without any additional catalysis (monitored by HPLC), an intermediate seems to be formed, associated with acylation at the nitrogen giving a quaternary ammonium salt. This salt is hydrolyzed by water which is added within the product isolation step, and the acid formed is decarboxylated immediately. The forming 1-phenyl-1,2,3,4-tetrahydroisoquinoline of formula VIII

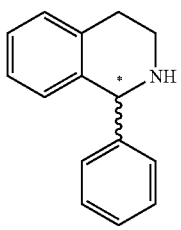

Formula VIII reacts immediately with the residue of the acylation agent (intermediate) giving, in a nearly quantitative yield, an urea according to the following Scheme 1.

Scheme 1

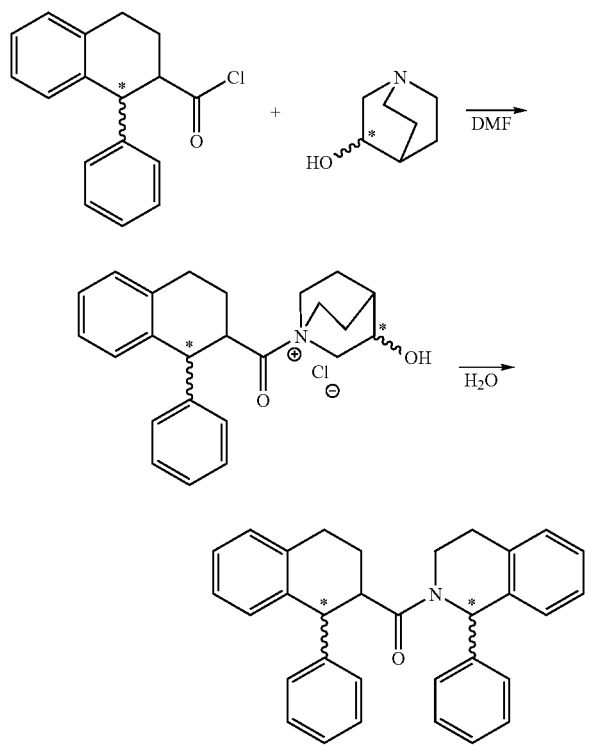

Furthermore, we have found experimentally that catalysis using an unbranched sodium alkoxide, as described in WO 2005/087231, is inconvenient because the unbranched alkoxide acts not only as a base but also as a nucleophilic agent, whereupon an impurity is formed—solifenacin substituted by an alkyl group in position 2 at the quinuclidine backbone.

DISCLOSURE OF INVENTION

The invention consists in a new procedure to prepare (1S)-(3R)-1-azabicyclo[2.2.2.]oct-3-yl 3,4-dihydro-1-phenyl-2(1H)-isoquinoline carboxylate, known under the nonproprietary name solifenacin, by condensation of (1S)-alkyl 1-phenyl-1,2,3,4-tetrahydro-2-isoquinoline carboxylate (where the alkyl is a primary $C_1$-$C_4$ alkyl) with 3-(R)-quinuclidol, the reaction being catalyzed by a non-nucleophilic base (Scheme 2).

Scheme 2

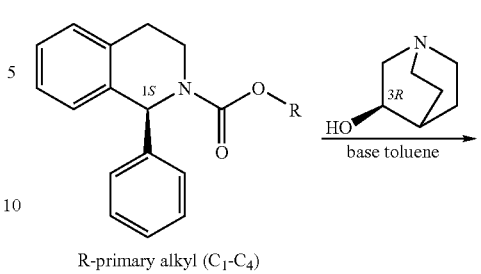

R-primary alkyl ($C_1$-$C_4$)

A non-nucleophilic base is a base whose nucleophilic substitution ability is limited significantly. Non-nucleophilic bases include, in particular, sterically hindered alcoholates ($C_4$-$C_6$) or amines; lithium compounds; or a group of substances known as phosphazenes. Examples of non-nucleophilic bases are given in Table 1 below.

TABLE 1

An overview of non-nucleophilic bases

| Abbreviation | Name |
| --- | --- |
| tBuLi | tert-Butyllithium |
|  | Hexyllithium |
| KOtBu | Potassium tert-butoxide |
| NaOtBu | Sodium tert-butoxide |
| LDA | Lithium diisopropylamide |
| K-HMDS | Potassium hexamethyldisalazide |
| Na-HMDS | Sodium hexamethyldisalazide |
| Li-HMDS | Lithium hexamethyldisalazide |
| Li-TMP | Lithium tetramethylpiperidide |
|  | 2,6-Di-tert-butyl-4-methylpyridine |
| TED | 1,4-Diazabicyclo(2.2.2)octane |
| MTBD | 7-Methyl-1,5,7-triazabicyclo(4.4.0)dec-5-ene |
| PMDBD | 3,3,6,9,9-Pentamethylpiperidin-2,10-diazabicyclo-(4.4.0)dec-1-ene |
| PMP | 1,2,2,6,6-Pentamethylpiperidine |
| TMG | 1,1,3,3-Tetramethylguanidine |
| TMP | 2,2,6,6-Tetramethylpiperidine |
| TBD | 1,5,7-Triazabicyclo(4.4.0)-dec-5-ene |
| DBU | 1,8-Diazabicyclo[5.4.0]undec-7-ene |
| DBN | 1,5-Diazabicyclo[4.3.0]non-5-ene |
| $P_1$-t-Bu base | N'-tert-butyl-N,N,N',N',N'',N''-hexamethylphosphorimidetriamide |
| BTPP | terc-Butylimino-tris(pyrrolidino) phosphorane |
| $P_1$-t-Oct base | tert-Octylimino-tris(dimethylamino) phosphorane |
| BEMP | 2-tert-Butylimino-2-diethylamino-1,3-dimethyl-perhydro-1,3,2-diazaphosphorine |
| $P_2$-t-Bu base | 1-terc-Butyl-2,2,4,4,4-pentakis(dimethylamino)-2-$\Lambda^5$,4 $\Lambda^5$-catenadi(phosphazene) |
| $P_2$-Et base | 1-Ethyl-2,2,4,4,4-pentakis(dimethylamino)-2-$\Lambda^5$,4 $\Lambda^5$-catenadi(phosphazene) |
| $P_4$-t-Bu base | 1-terc-Butyl-4,4,4-tris(dimethylamino)-2,2-bis[tris(dimethylamino)-phosphoranylidenamino]-2$\Lambda^5$,4$\Lambda^5$-catenadi(phosphazene) |

The following non-nucleophilic bases have appeared convenient for specific embodiments of the invention: potassium tert-butoxide; sodium tert-butoxide; tert-butyllithium; LDA; KHMDS; DBU; DBN; 2,6-di-tert-butyl-4-methylpyridine;

P$_1$-t-Bu base; BEMP; BTPP; and P$_2$-t-Bu base. From among those, potassium tert-butoxide, LDA, and DBU have been found to suit best.

With any one of the above three bases the conversion is nearly complete within 3 hours and no impurities such as have been described, for instance, in WO 2005/087231, are formed.

The present approach is convenient in that the transformation of (1S)-primary alkyl-1-phenyl-1,2,3,4-tetrahydro-2-isoquinoline carboxylate to solifenacin requires 3-(R)-quinuclidol in a small excess only. The excess is higher than or equal to the amount of the catalyst (non-nucleophilic base) employed to accelerate the reaction. In this setup the degree of conversion is sufficiently high and the degree of racemization of both the starting substances and the product is very low.

After the conversion is achieved, the reaction mixture is cooled and water is added. After phase separation, the aqueous phase is washed with toluene. The combined organic extracts are washed with water, brine, and water again. Subsequently, the toluene layer is evaporated to dryness. The crude evaporation residue is dissolved in methanol, and to the solution is added a solution of hydrochloric acid in methanol with the molar hydrogen chloride content equal to or slightly higher than the product content. Solifenacin HCl salt is isolated, which salt can be converted by conventional methods to any other organic or inorganic salt.

The principle of the invention is illustrated on the examples below.

EXAMPLES

Common features of Examples 1 through 6

To a solution of 1(S)-ethyl 1-phenyl-1,2,3,4-tetrahydro-2-isoquinoline carboxylate (0.1 mol) in toluene (25 ml) is added 3(R)-quinuclidol (0.1-0.15 mmol). The system is heated at 90° C., and after the two starting substances have dissolved completely, potassium tert-butanolate (0-0.05 mmol) is added to the constantly stirred mixture and the fine suspension formed is heated to boil. While the reaction proceeds, the azeotropic toluene-ethanol mixture is distilled off from the mixture. The reaction is terminated after reaching the appropriate degree of conversion.

The development of the reaction (conversion of the substances) was monitored by gas chromatography.

The optical purity of the product was determined by capillary electrophoresis.

The analytical results for the products prepared as specified in Examples 1-6 are given in the table below.

Example 7

To a solution of 1(S)-ethyl 1-phenyl-1,2,3,4-tetrahydro-2-isoquinoline carboxylate (19.2 mol) in toluene (140 ml) was added 3(R)-quinuclidol (23.04 mmol). The system was heated at 90° C., and after the two starting substances had dissolved completely, potassium tert-butanolate (3.84 mmol) was added to the constantly stirred mixture and the fine suspension formed was heated to boil. While the reaction proceeded, the azeotropic toluene-ethanol mixture was distilled off from the mixture. The reaction was terminated after 3 hours of boil, when GC indicated that a 97% degree of conversion had been reached. A volume of 50 ml of water was added and the mixture was stirred at room temperature for 20 minutes. The toluene layer was allowed to separate in a separating funnel and the aqueous layer was washed with toluene (2×50 ml). The combined organic extracts were washed with 50 ml of water, 25 ml of brine, and 25 ml of water, and evaporated to dryness on a rotary vacuum evaporator. The crude evaporation residue was dissolved in methanol, a solution of hydrochloric acid in methanol was added, and the whole was evaporated to dryness in a rotary vacuum evaporator. The product was obtained in the form of a white solid (4.54 g, 68.79% theory).

Example 8

To a solution of 1(S)-ethyl 1-phenyl-1,2,3,4-tetrahydro-2-isoquinoline carboxylate (3.6 mol) in toluene (30 ml) was added 3(R)-quinuclidol (4.3 .mmol). The system was heated at 90° C., and after the two starting substances had dissolved completely, a 1.8 M solution of lithium diisopropylamide in a THF-heptane-EtOH mixture (0.7 mmol) was added to the constantly stirred mixture, and the whole was heated to boil. While the reaction proceeded, the azeotropic toluene-ethanol mixture was distilled off from the mixture. The reaction was terminated after 6 hours of boil. The mixture was processed conventionally to obtain the product as the HCl salt. Yield of the white crystalline substance: 420 mg (29.2% theory).

Example 9

To a solution of 1(S)-ethyl 1-phenyl-1,2,3,4-tetrahydro-2-isoquinoline carboxylate (3.6 mol) in toluene (30 ml) was added 3(R)-quinuclidol (4.3 .mmol). The system was heated at 90° C., and after the two starting substances had dissolved completely, 1,8-diazabicyclo[5.4.0]undec-7-ene (DBU) (0.7 mmol) was added to the constantly stirred mixture, and the whole was heated to boil. While the reaction proceeded, the azeotropic toluene-ethanol mixture was distilled off from the

|  | Starting substances (%) | | Percent existing in | | | | | | | | | | | | | |
|---|---|---|---|---|---|---|---|---|---|---|---|---|---|---|---|---|
|  |  |  | 3 hours | | | 4 hours | | | 5 hours | | | 6 hours | | | 10 hours | | |
| Batch | Quin | tBOC | conv. | R,R | S,S | conv. | R,R | S,S | conv. | R,R | S,S | conv. | R,R | S,S | conv. | R,R | S,S |
| 9-142 | 120 | 20 | 96.11 | 1.77 | 1.97 | 96.45 | 2.07 | 2.27 | 97.07 | 2.27 | 2.27 | — | — | — | — | — | — |
| 9-143 | 110 | 10 | 51.29 | 0.21 | 0.50 | 78.20 | 1.32 | 0.78 | 87.45 | 1.82 | 0.95 | 95.86 | 5.12 | 1.42 | 96.07 | 5.13 | 1.51 |
| 9-144 | 110 | 20 | 96.80 | 5.12 | 2.33 | — | — | — | — | — | — | — | — | — | — | — | — |
| 9-145 | 130 | 20 | 87.52 | 2.15 | 0.78 | — | — | — | — | — | — | — | — | — | — | — | — |
| 9-146 | 120 | 30 | 96.01 | 4.56 | 1.38 | — | — | — | — | — | — | — | — | — | — | — | — |
| 9-148 | 130 | 10 | 34.53 | 0.00 | 0.00 | — | — | — | 64.93 | 0.40 | 0.48 | 76.45 | 0.58 | 0.75 | — | — | — | mixture. The reaction was terminated after 6 hours of boil. The mixture was processed conventionally to obtain the product as the HCl salt.

The yield of the white crystalline substance obtained was 400 mg (27.8% theory).

The invention claimed is:

1. A process for the preparation of (1S)-(3R)-1-azabicyclo[2.2.2.]oct-3-yl 3,4-dihydro-1-phenyl-2(1H)-isoquinoline carboxylate by reacting (1S)-alkyl-1-phenyl-1,2,3,4-tetrahydro-2-isoquinoline carboxylate with 3-(R)-quinuclidol in an inert solvent, wherein a primary alkyl ester of the carboxylate whose alkyl length is $C_1$-$C_4$ is used and the reaction is catalyzed by a non-nucleophilic base selected from the group consisting of potassium tert-butanolate and sodium tert-butanolate, wherein the reaction is conducted in toluene at a temperature of the reaction mixture of 90° C. to 120° C., using 3-(R)-quinuclidol in a 0% to 50% molar excess with respect to (1S)-alkyl 1-phenyl-1,2,3,4-tetrahydro-2-isoquinoline carboxylate, and using 0% to 50% mol of the catalyst with respect to (1S)-alkyl 1-phenyl-1,2,3,4-tetrahydro-2-isoquinoline carboxylate.

2. The process as claimed in claim 1, wherein the molar amount of the catalyst is lower than the molar excess of 3-(R)-quinuclidol with respect to (1S)-alkyl 1-phenyl-1,2,3,4-tetrahydro-2-isoquinoline carboxylate.

3. The process as claimed in claim 1, wherein the primary alkyl ester is selected from the group of (1S)-alkyl 1-phenyl-1,2,3,4-tetrahydro-2-isoquinoline carboxylates.

* * * * *